US012642605B2

(12) United States Patent
Naclerio

(10) Patent No.: US 12,642,605 B2
(45) Date of Patent: Jun. 2, 2026

(54) POWER DISTRIBUTION IN A SURGICAL ROBOTIC SYSTEM

(71) Applicant: Covidien LP, Mansfield, MA (US)

(72) Inventor: Edward J. Naclerio, Madison, CT (US)

(73) Assignee: Covidien LP, Mansfield, MA (US)

( * ) Notice: Subject to any disclaimer, the term of this patent is extended or adjusted under 35 U.S.C. 154(b) by 728 days.

(21) Appl. No.: 17/791,378

(22) PCT Filed: Jan. 19, 2021

(86) PCT No.: PCT/US2021/013854
§ 371 (c)(1),
(2) Date: Jul. 7, 2022

(87) PCT Pub. No.: WO2021/158354
PCT Pub. Date: Aug. 12, 2021

(65) Prior Publication Data
US 2023/0033915 A1    Feb. 2, 2023

Related U.S. Application Data

(60) Provisional application No. 62/970,783, filed on Feb. 6, 2020.

(51) Int. Cl.
A61B 34/30 (2016.01)
(52) U.S. Cl.
CPC ...... A61B 34/30 (2016.02); A61B 2560/0204 (2013.01); A61B 2560/0443 (2013.01)
(58) Field of Classification Search
CPC .... A61B 2560/0204; A61B 2560/0214; A61B 2560/0276; A61B 2560/0443; A61B 34/30; A61B 50/13; H02J 2310/23; H02J 9/06
See application file for complete search history.

(56) References Cited

U.S. PATENT DOCUMENTS 6,527,721 B1    3/2003  Wittrock et al.
9,680,333 B1    6/2017  Brooks et al.
(Continued)

FOREIGN PATENT DOCUMENTS

EP        2533130 A1    12/2012
WO    2020210106 A1    10/2020

OTHER PUBLICATIONS

International Search Report and Written Opinion dated May 19, 2021 issued in corresponding PCT Appln. No. PCT/US2021/013854.
(Continued)

*Primary Examiner* — Tameem D Siddiquee
(74) *Attorney, Agent, or Firm* — Carter, DeLuca & Farrell, LLP

(57)    ABSTRACT

A surgical robotic system including at least one movable cart including a robotic arm having a surgical instrument is disclosed. The system further includes a control tower having at least one component and a power supply system coupled to the at least one movable cart via a cable. The power supply system includes: a tower power supply chassis configured to supply first direct current to the at least one movable cart; a power distribution unit configured to supply second direct current to the at least one component; a first uninterruptable power supply coupled to the tower power supply chassis; and a second uninterruptable power supply coupled to the power distribution unit. The control tower further includes a startup controller configured to control the power supply system to transition between a plurality of power stages.

20 Claims, 6 Drawing Sheets

(56) References Cited

U.S. PATENT DOCUMENTS

| | | | | |
|---|---|---|---|---|
| 2005/0174218 | A1* | 8/2005 | Jordan | B60R 25/1003 |
| | | | | 340/426.1 |
| 2007/0114852 | A1 | 5/2007 | Lin et al. | |
| 2014/0133201 | A1* | 5/2014 | Brandmeyer | H02J 9/061 |
| | | | | 363/65 |
| 2015/0344051 | A1* | 12/2015 | Lenkman | B62B 3/02 |
| | | | | 248/638 |
| 2017/0251990 | A1* | 9/2017 | Kheradpir | A61B 50/13 |
| 2019/0069962 | A1 | 3/2019 | Tabandeh et al. | |
| 2019/0109487 | A1* | 4/2019 | O'Toole | H04W 52/0203 |
| 2019/0231460 | A1 | 8/2019 | DiMaio et al. | |
| 2021/0212779 | A1* | 7/2021 | Zheng | A61B 34/74 |

OTHER PUBLICATIONS

Examination Report issued in corresponding application EP21705329.7 dated Jun. 27, 2025.

* cited by examiner

POWER DISTRIBUTION IN A SURGICAL ROBOTIC SYSTEM

CROSS REFERENCE TO RELATED APPLICATIONS

The present application is a National Stage Application under 35 U.S.C. § 371(a) of PCT/US2021/13854, filed Jan. 19, 2021, which claims the benefit of and priority to U.S. Patent Provisional Application No. filed 62/970,783 filed on Feb. 6, 2020. The entire disclosures of the foregoing applications are incorporated by reference herein.

BACKGROUND

Surgical robotic systems are currently being used in minimally invasive medical procedures. Some surgical robotic systems include a surgical console controlling a surgical robotic arm and a surgical instrument having an end effector (e.g., forceps or grasping instrument) coupled to and actuated by the robotic arm. Such robotic systems are powered by complex electrical power supply systems with multiple electrical supply rails and backup units. Thus, there is a need for a streamlined power management for surgical robotic systems to control complex electrical power supplies.

SUMMARY

The present disclosure provides a surgical robotic system including a plurality of components, namely, a control tower, a console, and one or more surgical robotic arms, each of which is disposed on a movable cart and includes a surgical instrument. The control tower includes a power supply system which distributes power to each of the movable carts and their respective robotic arms attached thereto. The power supply system includes a plurality of uninterruptible power supplies ("UPS") which provide backup power to various components of the surgical robotic system. One of the UPSs provides power to the movable carts and their respective surgical robotic arms and another UPS powers various components of the control tower, such as network switches, computers, and the like. The control tower includes a startup controller which coordinates an activation/deactivation sequence for the control tower and, by extension, the entire surgical robotic system by controlling the control tower and the UPSs through one of three stages. In the first stage the control tower is in an idle state, in a second stage the control tower and the surgical robotic system are in active state and ready to perform surgery, and in a third stage the control tower is in a shutdown state.

According to one embodiment of the present disclosure, a surgical robotic system including at least one movable cart including a robotic arm having a surgical instrument is disclosed. The system further includes a control tower having at least one component and a power supply system coupled to the at least one movable cart via a cable. The power supply system includes: a tower power supply chassis configured to supply first direct current to the at least one movable cart; a power distribution unit configured to supply second direct current to the at least one component; a first uninterruptable power supply coupled to the tower power supply chassis; and a second uninterruptable power supply coupled to the power distribution unit. The control tower further includes a startup controller configured to control the power supply system to transition between a plurality of power stages.

According to one aspect of the above embodiment, the control tower further includes a display configured to display a graphical user interface and a communication interface coupled to at least one input device. The power stages include a first idle stage, a second active stage, and a third shutdown stage. The second uninterruptable power supply includes a first output and a second output, wherein the first output of the second uninterruptable power supply is coupled to the power distribution unit and the second output of the second uninterruptable power supply is coupled to the startup controller, the display, and the communication interface. During the first idle stage the startup controller is configured to activate an output of the first uninterruptable power supply coupled to the tower power supply chassis and the first output of the second uninterruptable power supply.

According to another aspect of the above embodiment, the control tower is coupled to a first alternating current input that is coupled to the first uninterruptable power supply and a second alternating current input that is coupled to the second uninterruptable power supply. The startup controller is further configured to detect disconnection of the first alternative current input and the second alternating current input. The startup controller is further configured to shut off the first uninterruptable power supply and the second uninterruptable power supply in response to detection of the disconnection. The startup controller is also configured to output an alarm on the display. The startup controller is yet further configured to switch from the first idle stage to the second active stage in response to a user input.

According to a further aspect of the above embodiment, during the second active stage, the startup controller is further configured to activate the first output of the second uninterruptable power supply to power up the power distribution unit. During the third shutdown stage, the startup controller is further configured to display a graphical user interface of instructions for disconnecting the at least one movable cart from the control tower. The startup controller is also configured to shutoff the output of the first uninterruptable power supply coupled to the tower power supply chassis and the first output of the second uninterruptable power supply coupled to the power distribution unit.

According to another embodiment of the present disclosure, a surgical robotic system is disclosed. The surgical robotic system includes at least one movable cart including a robotic arm having a surgical instrument and a control tower coupled to a first alternating current input and a second alternating current input. The control tower includes: at least one component and a power supply system coupled to the at least one movable cart via a cable. The power supply system includes: a tower power supply chassis configured to supply first direct current to the at least one movable cart; a power distribution unit configured to supply second direct current to the at least one component; a first uninterruptable power supply coupled to the first alternating current input and including a first output configured to power the tower power supply chassis; and a second uninterruptable power supply coupled to the second alternating current input and including a first output configured to power the power distribution unit. The control tower further includes a startup controller configured to control the power supply system to transition between a first idle stage, a second active stage, and a third shut down stage.

According to one aspect of the above embodiment, the control tower further includes a display configured to display a graphical user interface and a communication interface coupled to at least one input device. The second uninterruptable power supply includes a second output that is coupled to the startup controller, the display, and the communication interface. The startup controller is further configured to detect disconnection of the first alternative current input and the second alternating current input. The startup controller is also configured to shut off the first uninterruptable power supply and the second uninterruptable power supply in response to detection of the disconnection. The startup controller is yet further configured to output an alarm on the display and to transition to the first idle stage.

BRIEF DESCRIPTION OF THE DRAWINGS

Embodiments of the present disclosure are described herein with reference to the accompanying drawings, wherein.

DETAILED DESCRIPTION

Figure 1:
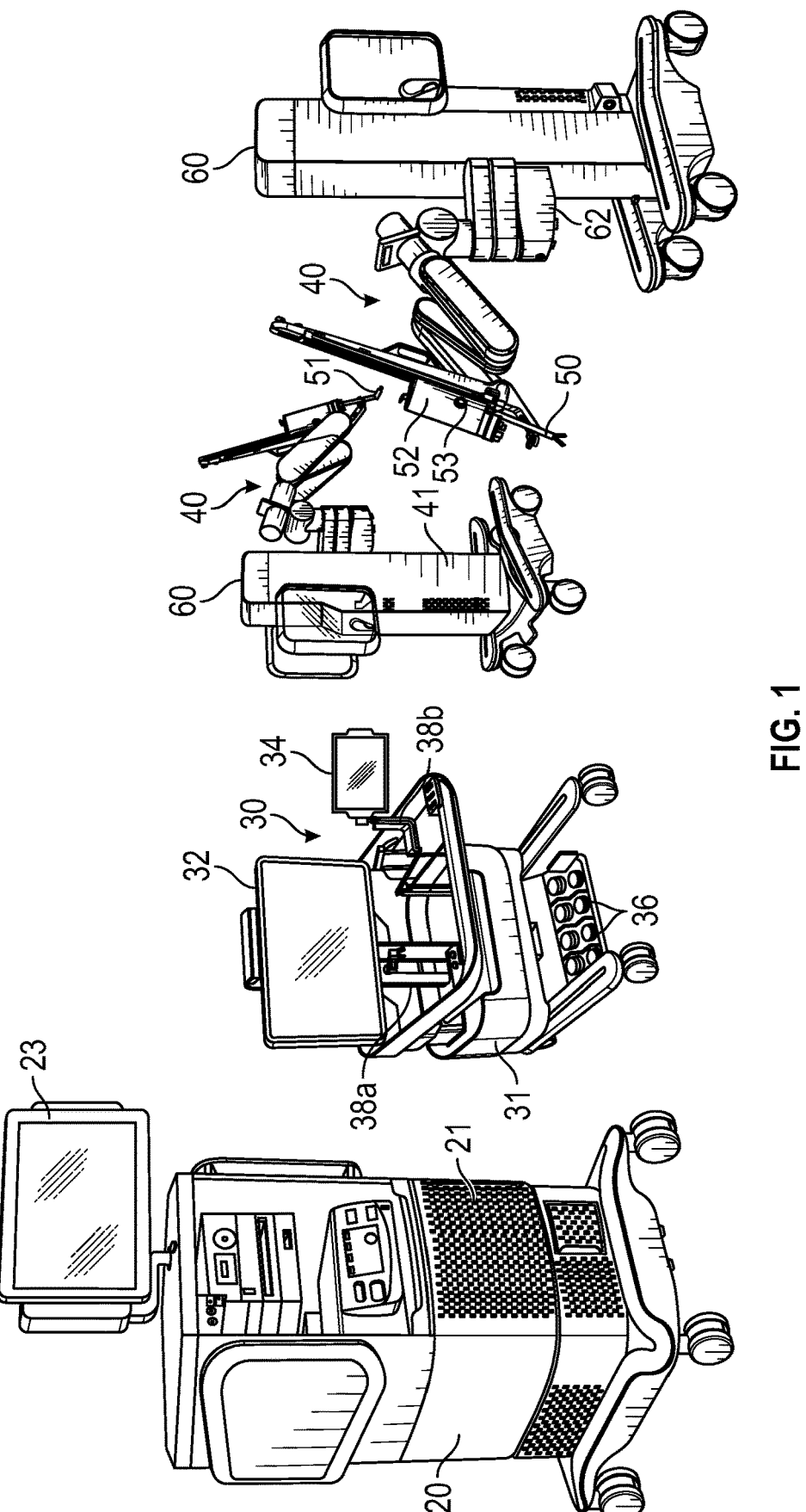
FIG. 1 is a schematic illustration of a surgical robotic system including a control tower, a console, and one or more surgical robotic arms according to the present disclosure.

Embodiments of the presently disclosed surgical robotic system are described in detail with reference to the drawings, in which like reference numerals designate identical or corresponding elements in each of the several views. As used herein the term "distal" refers to the portion of the surgical robotic system and/or the surgical instrument coupled thereto that is closer to the patient, while the term "proximal" refers to the portion that is farther from the patient.

The term "application" may include a computer program designed to perform functions, tasks, or activities for the benefit of a user. Application may refer to, for example, software running locally or remotely, as a standalone program or in a web browser, or other software which would be understood by one skilled in the art to be an application. An application may run on a controller, or on a user device, including, for example, a mobile device, an IOT device, or a server system.

As will be described in detail below, the present disclosure is directed to a surgical robotic system, which includes a surgical console, a control tower, and one or more movable carts having a surgical robotic arm coupled to a setup arm. The surgical console receives user input through one or more interface devices, which are interpreted by the control tower as movement commands for moving the surgical robotic arm. The surgical robotic arm includes a controller, which is configured to process the movement command and to generate a torque command for activating one or more actuators of the robotic arm, which would, in turn, move the robotic arm in response to the movement command.

With reference to FIG. 1, a surgical robotic system 10 includes a control tower 20, which is connected to all of the components of the surgical robotic system 10 including a surgical console 30 and one or more robotic arms 40. Each of the robotic arms 40 includes a surgical instrument 50 removably coupled thereto. Each of the robotic arms 40 is also coupled to a movable cart 60.

The surgical instrument 50 is configured for use during minimally invasive surgical procedures. In embodiments, the surgical instrument 50 may be configured for open surgical procedures. In embodiments, the surgical instrument 50 may be an endoscope configured to provide a video feed for the user. In further embodiments, the surgical instrument 50 may be an electrosurgical forceps configured to seal tissue by compression tissue between jaw members and applying electrosurgical current thereto. In yet further embodiments, the surgical instrument 50 may be a surgical stapler including a pair of jaws configured to grasp and clamp tissue whilst deploying a plurality of tissue fasteners, e.g., staples, and cutting stapled tissue.

Each of the robotic arms 40 may include a camera 51 configured to capture video of the surgical site. The camera 51 may be a stereoscopic camera and may be disposed along with the surgical instrument 50 on the robotic arm 40. The surgical console 30 includes a first display 32, which displays a video feed of the surgical site provided by camera 51 of the surgical instrument 50 disposed on the robotic arms 40, and a second display device 34, which displays a user interface for controlling the surgical robotic system 10. The surgical console 30 also includes a plurality of user interface devices, such as foot pedals 36 and a pair of handle controllers 38a and 38b which are used by a user to remotely control robotic arms 40.

The control tower 20 includes a display 23, which may be a touchscreen, and outputs on the graphical user interfaces (GUIs). The control tower 20 also acts as an interface between the surgical console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgical console 30, in such a way that robotic arms 40 and the surgical instrument 50 execute a desired movement sequence in response to input from the foot pedals 36 and the handle controllers 38a and 38b.

Each of the control tower 20, the surgical console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 802.15.4-2003 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
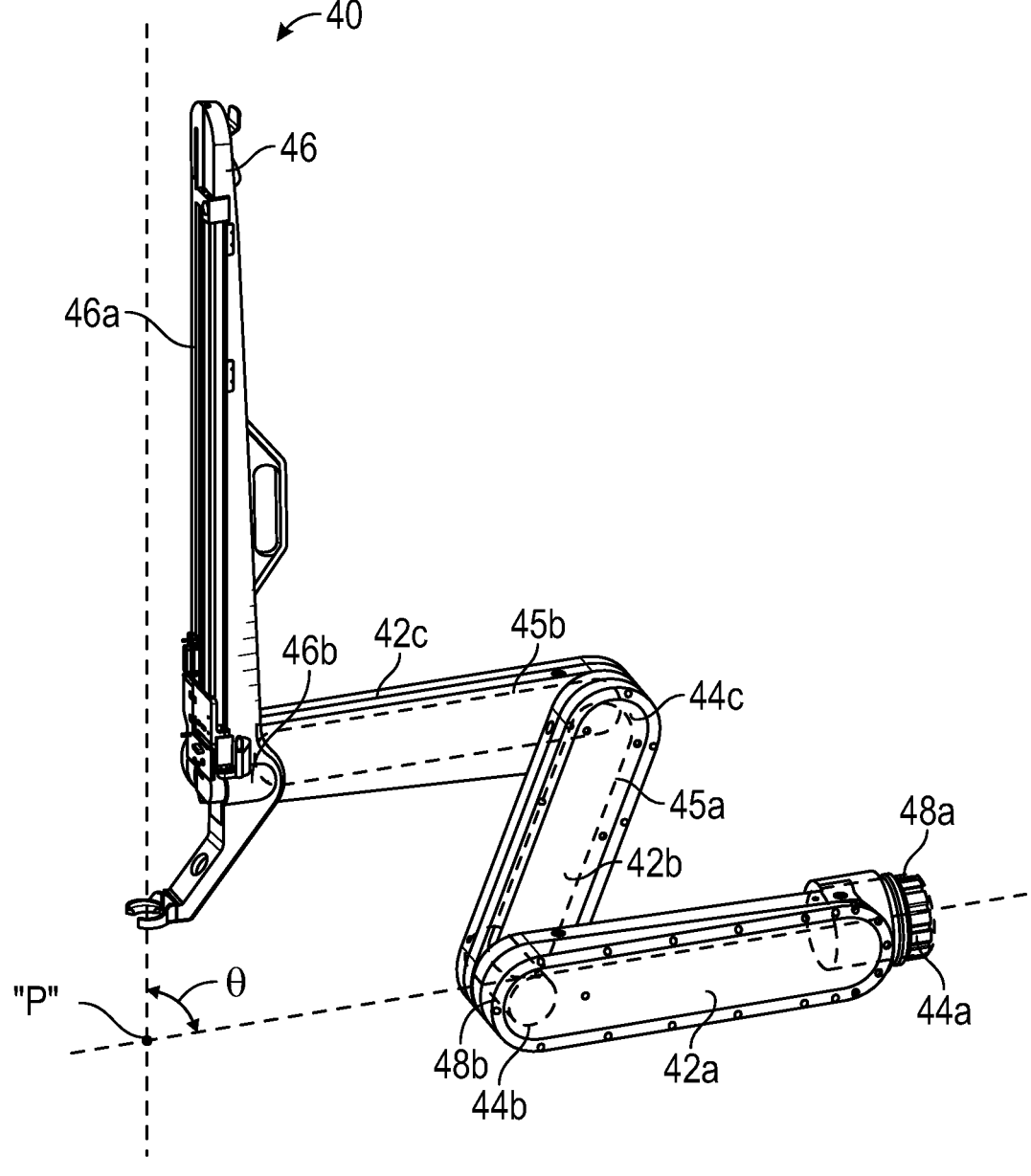
FIG. 2 is a perspective view of a surgical robotic arm of the surgical robotic system of FIG. 1 according to the present disclosure.
Figure 3:
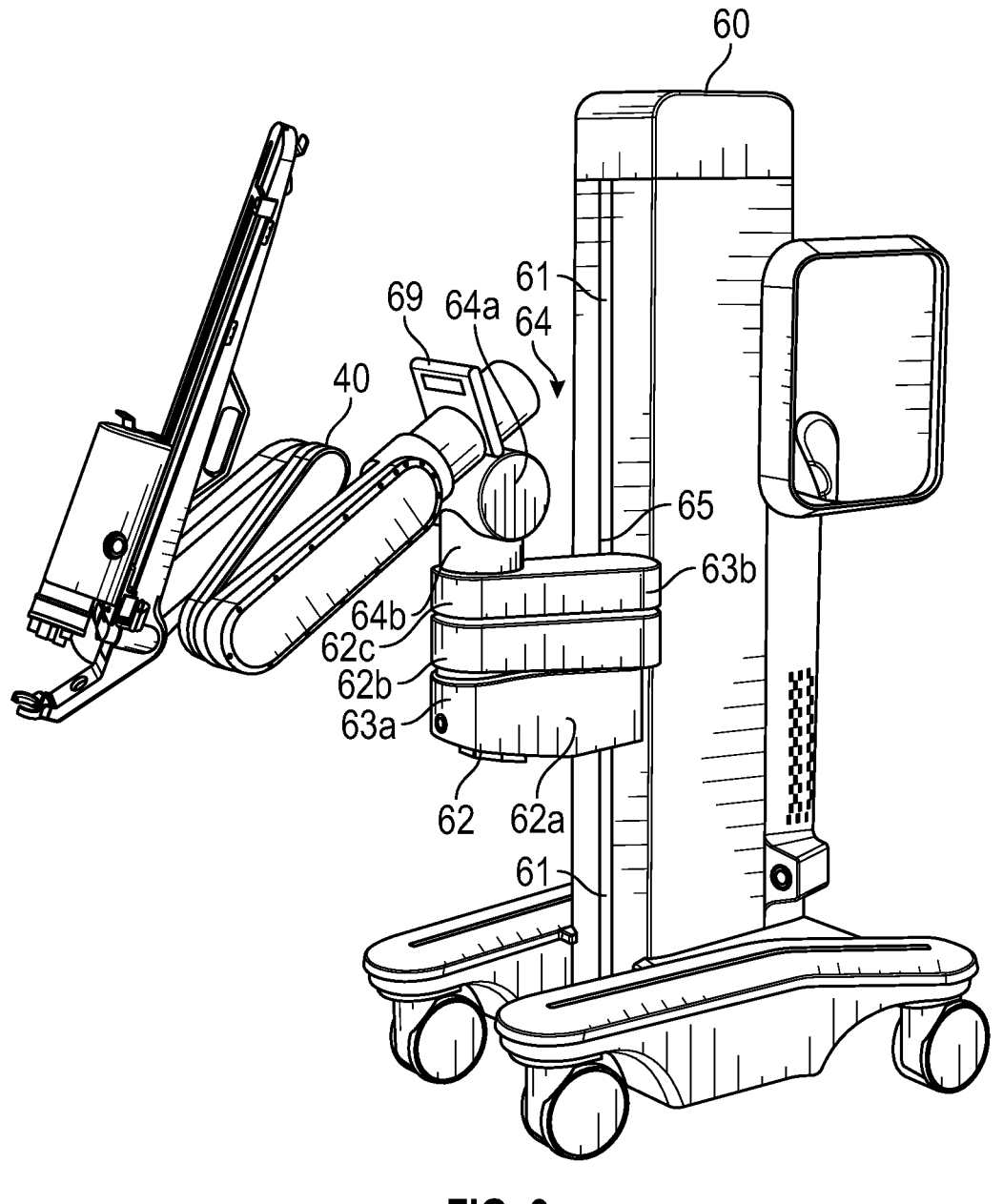
FIG. 3 is a perspective view of a setup arm with the surgical robotic arm of the surgical robotic system of FIG. 1 according to the present disclosure.

With reference to FIG. 2, each of the robotic arms 40 may include a plurality of links 42a, 42b, 42c, which are interconnected at joints 44a, 44b, 44c, respectively. The joint 44a is configured to secure the robotic arm 40 to the movable cart 60 and defines a first longitudinal axis. With reference to FIG. 3, the movable cart 60 includes a lift 61 and a setup arm 62, which provides a base for mounting of the robotic arm 40. The lift 61 allows for vertical movement of the setup arm 62. The movable cart 60 also includes a display 69 for displaying information pertaining to the robotic arm 40.

The setup arm 62 includes a first link 62a, a second link 62b, and a third link 62c, which provide for lateral maneuverability of the robotic arm 40. The links 62a, 62b, 62c are interconnected at joints 63a and 63b, each of which may include an actuator (not shown) for rotating the links 62b and 62b relative to each other and the link 62c. In particular, the links 62a, 62b, 62c are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 62 includes controls 65 for adjusting movement of the links 62a, 62b, 62c as well as the lift 61.

The third link 62c includes a rotatable base 64 having two degrees of freedom. In particular, the rotatable base 64 includes a first actuator 64a and a second actuator 64b. The first actuator 64a is rotatable about a first stationary arm axis which is perpendicular to a plane defined by the third link 62c and the second actuator 64b is rotatable about a second stationary arm axis which is transverse to the first stationary arm axis. The first and second actuators 64a and 64b allow for full three-dimensional orientation of the robotic arm 40.

The robotic arm 40 also includes a plurality of manual override buttons 53 disposed on instrument drive unit 52 and the setup arm 62, which may be used in a manual mode. The user may press one or the buttons 53 to move the component associated with the button 53.

With reference to FIG. 2, the robotic arm 40 also includes a holder 46 defining a second longitudinal axis and configured to receive the instrument drive unit 52 (FIG. 1) of the surgical instrument 50, which is configured to couple to an actuation mechanism of the surgical instrument 50. Instrument drive unit 52 transfers actuation forces from its actuators to the surgical instrument 50 to actuate components (e.g., end effectors) of the surgical instrument 50. The holder 46 includes a sliding mechanism 46a, which is configured to move the instrument drive unit 52 along the second longitudinal axis defined by the holder 46. The holder 46 also includes a joint 46b, which rotates the holder 46 relative to the link 42c.

The joints 44a and 44b include an actuator 48a and 48b configured to drive the joints 44a, 44b, 44c relative to each other through a series of belts 45a and 45b or other mechanical linkages such as a drive rod, a cable, or a lever and the like. In particular, the actuator 48a is configured to rotate the robotic arm 40 about a longitudinal axis defined by the link 42a.

The actuator 48b of the joint 44b is coupled to the joint 44c via the belt 45a, and the joint 44c is in turn coupled to the joint 46c via the belt 45b. Joint 44c may include a transfer case coupling the belts 45a and 45b, such that the actuator 48b is configured to rotate each of the links 42b, 42c and the holder 46 relative to each other. More specifically, links 42b, 42c, and the holder 46 are passively coupled to the actuator 48b which enforces rotation about a pivot point "P" which lies at an intersection of the first axis defined by the link 42a and the second axis defined by the holder 46. Thus, the actuator 48b controls the angle θ between the first and second axes allowing for orientation of the surgical instrument 50. Due to the interlinking of the links 42a, 42b, 42c, and the holder 46 via the belts 45a and 45b, the angles between the links 42a, 42b, 42c, and the holder 46 are also adjusted in order to achieve the desired angle θ. In embodiments, some or all of the joints 44a, 44b, 44c may include an actuator to obviate the need for mechanical linkages.

Figure 4:
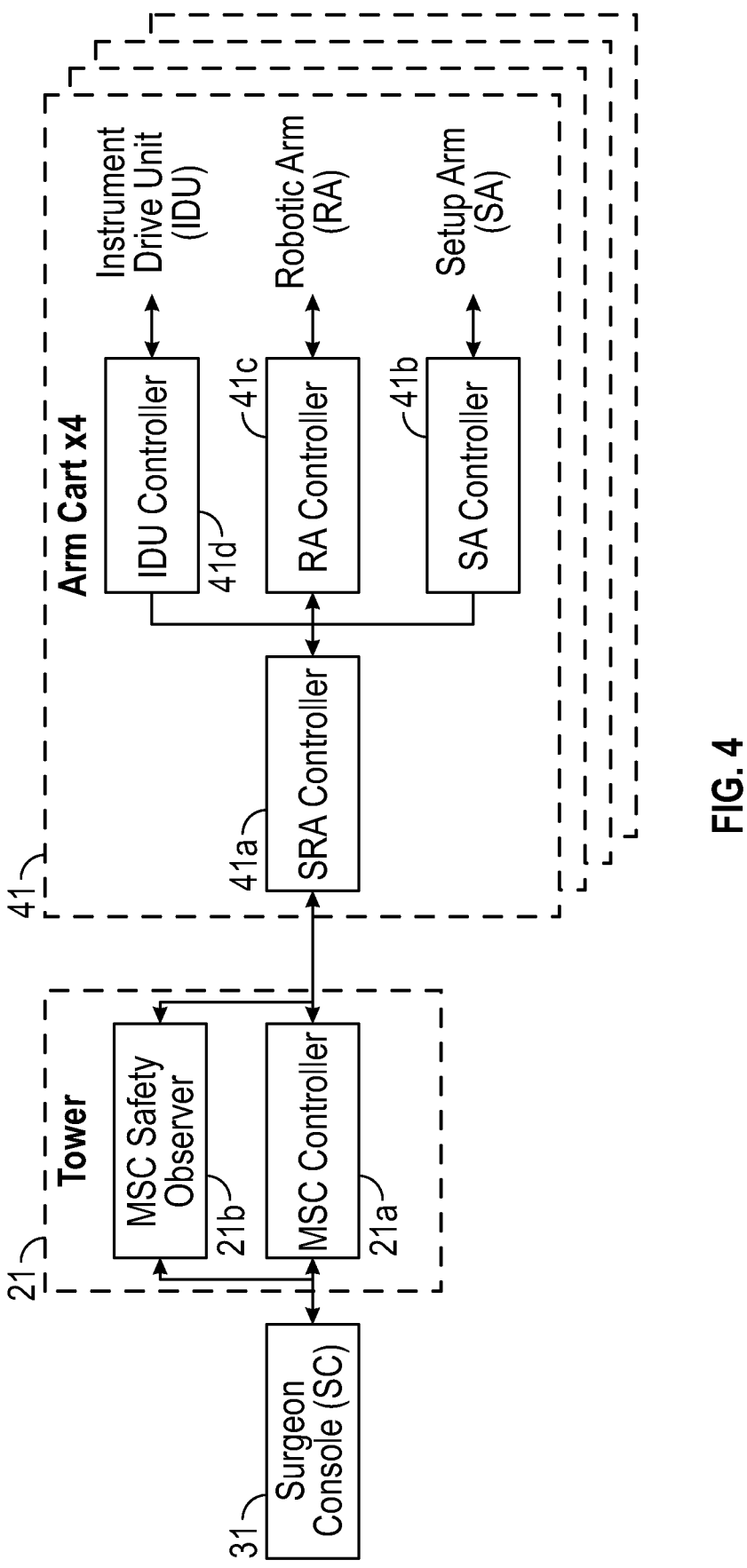
FIG. 4 is a schematic diagram of a computer architecture of the surgical robotic system of FIG. 1 according to the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21a and safety observer 21b. The controller 21a receives data from the computer 31 of the surgical console 30 about the current position and/or orientation of the handle controllers 38a and 38b and the state of the foot pedals 36 and other buttons. The controller 21a processes these input positions to determine desired drive commands for each joint of the robotic arm 40 and/or the instrument drive unit 52 and communicates these to the computer 41 of the robotic arm 40. The controller 21a also receives back the actual joint angles and uses this information to determine force feedback commands that are transmitted back to the computer 31 of the surgical console 30 to provide haptic feedback through the handle controllers 38a and 38b. The safety observer 21b performs validity checks on the data going into and out of the controller 21a and notifies a system fault handler if errors in the data transmission are detected to place the computer 21 and/or the surgical robotic system 10 into a safe state.

The computer 41 includes a plurality of controllers, namely, a main cart controller 41a, a setup arm controller 41b, a robotic arm controller 41c, and an instrument drive unit (IDU) controller 41d. The main cart controller 41a receives and processes joint commands from the controller 21a of the computer 21 and communicates them to the setup arm controller 41b, the robotic arm controller 41c, and the IDU controller 41d. The main cart controller 41a also manages instrument exchanges and the overall state of the movable cart 60, the robotic arm 40, and the instrument drive unit 52. The main cart controller 41a also communicates actual joint angles back to the controller 21a.

The setup arm controller 41b controls each of joints 63a and 63b, and the rotatable base 64 of the setup arm 62 and calculates desired motor movement commands (e.g., motor torque) for the pitch axis and controls the brakes. The robotic arm controller 41c controls each joint 44a and 44b of the robotic arm 40 and calculates desired motor torques required for gravity compensation, friction compensation, and closed loop position control of the robotic arm 40. The robotic arm controller 41c calculates a movement command based on the calculated torque. The calculated motor commands are then communicated to one or more of the actuators 48a and 48b in the robotic arm 40. The actual joint positions are then transmitted by the actuators 48a and 48b back to the robotic arm controller 41c.

The IDU controller 41d receives desired joint angles for the surgical instrument 50, such as wrist and jaw angles, and computes desired currents for the motors in the instrument drive unit 52. The IDU controller 41d calculates actual angles based on the motor positions and transmits the actual angles back to the main cart controller 41a.

The robotic arm 40 is controlled as follows. Initially, a pose of the handle controller controlling the robotic arm 40, e.g., the handle controller 38a, is transformed into a desired pose of the robotic arm 40 through a hand eye transform function executed by the controller 21a. The hand eye function, as well as other functions described herein, is/are embodied in software executable by the controller 21a or any other suitable controller described herein. The pose of one of the handle controller 38a may be embodied as a coordinate position and role-pitch-yaw ("RPY") orientation relative to a coordinate reference frame, which is fixed to the surgical console 30. The desired pose of the instrument 50 is relative to a fixed frame on the robotic arm 40. The pose of the handle controller 38a is then scaled by a scaling function executed by the controller 21a. In embodiments, the coordinate position is scaled down and the orientation is scaled up by the scaling function. In addition, the controller 21a also executes a clutching function, which disengages the handle controller 38a from the robotic arm 40. In particular, the controller 21a stops transmitting movement commands from the handle controller 38a to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38a and is then passed by an inverse kinematics function executed by the controller 21a. The inverse kinematics function calculates angles for the joints 44a, 44b, 44c of the robotic arm 40 that achieve the scaled and adjusted pose input by the handle controller 38a. The calculated angles are then passed to the robotic arm controller 41c, which includes a joint axis controller having a proportional-derivative (PD) controller, the friction estimator module, the gravity compensator module, and a two-sided saturation block, which is configured to limit the commanded torque of the motors of the joints 44a, 44b, 44c.

Figure 5:
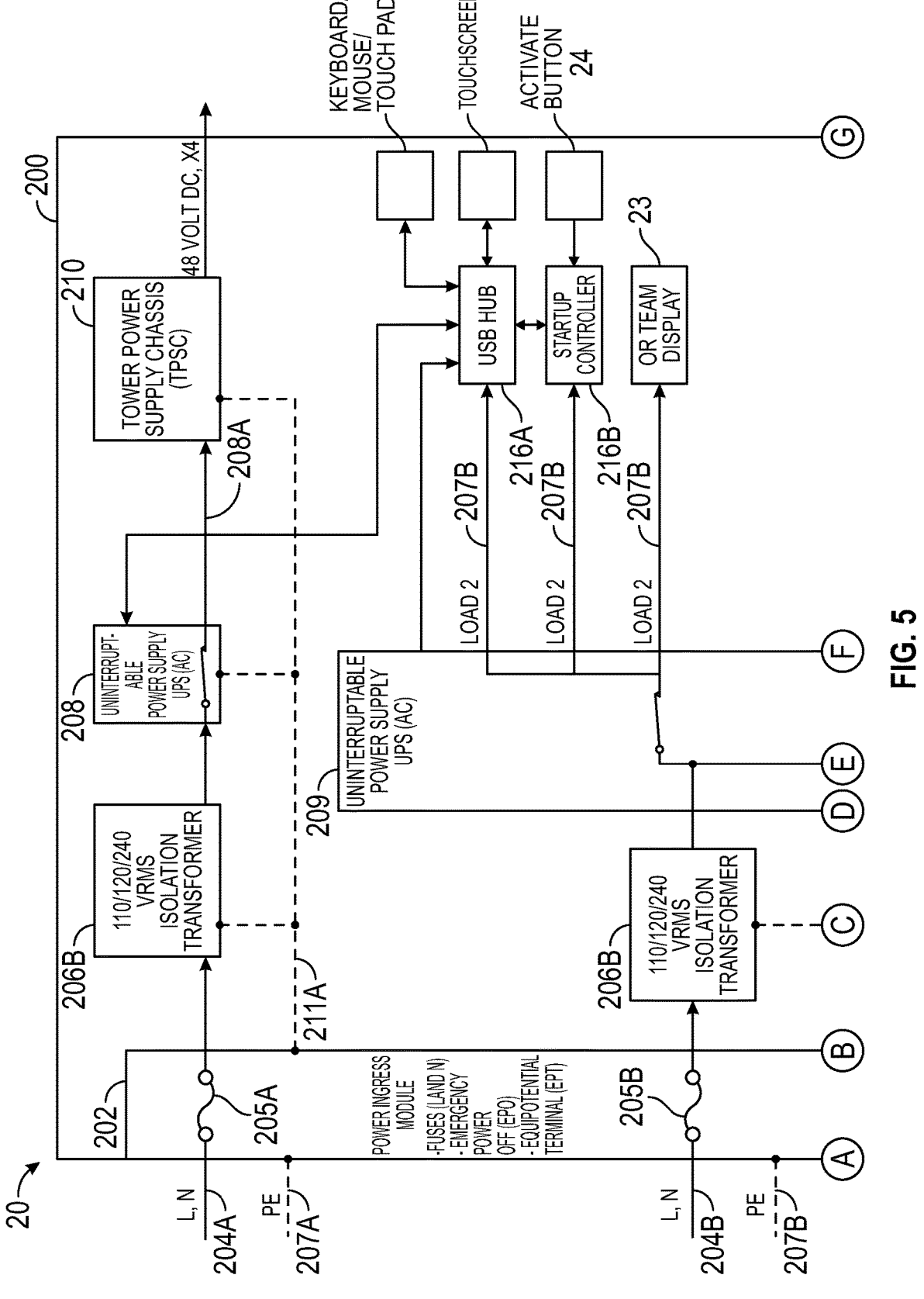
FIG. 5 is a schematic electrical circuit diagram of a power supply according to the present disclosure.
Figure 5:
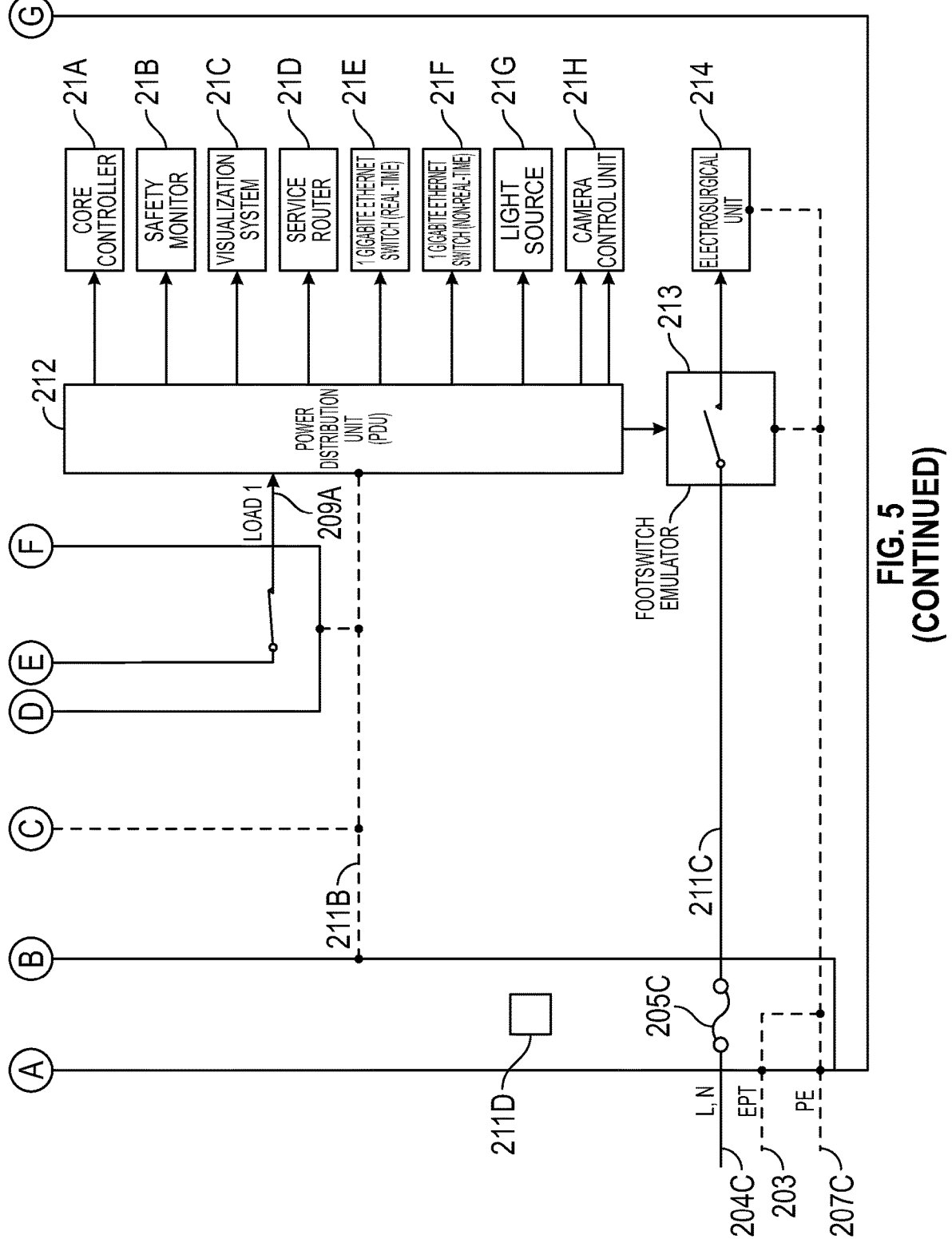

With reference to FIG. 5, the robotic system 10 includes a power supply system 200 housed in the control tower 20. Each of movable carts 60 is electrically coupled to the power supply system 200. The power supply system 200 includes a power ingress module 202, which is coupled to one or more AC line inputs 204a, 204b, 204c. Each of the AC line inputs 204a-c includes line and neutral connections which are coupled to each other through a fuse 205a, 205b, 205c, respectively, to provide for overcurrent protection. In addition, each of the AC line inputs 204a-c also includes a protective earth connection 207a, 207b, 207c, respectively. The power ingress module 202 also includes an equipotential terminal 203 to provide for common ground.

Each of the AC line inputs 204a and 204b is also coupled to a corresponding isolation transformer 206a and 206b of the power supply system 200 and the control tower 20, respectively, for electrical safety purposes and to uninterruptible power supplies ("UPS") 208 and 209, which provide backup electrical power to various components. In particular, the UPSs 208 and 209 are coupled to a tower power supply chassis ("TPSC") 210 and power distribution unit ("PDU") 212, respectively.

Each of the UPSs 208 and 209 may have multiple, independently controllable, AC power outputs, such as outputs 208a, 209a, and 209b. In particular, the UPS 208 supplies power to the TPSC 210 through the output 208a. The TPSC 210 is configured to couple to the movable cart 60 such that the TPSC 210 outputs a direct current, which powers motors and other electromechanical actuators of the robotic arm 40 and the movable cart 60.

The UPS 209 has two power outputs 209a and 209b. The output 209b supplies power to electronic components of the control tower 20, such as a communication interface 216a (e.g., a USB hub) coupled to various peripheral input devices (e.g., keyboard, touchpad, mouse, touchscreen, etc.), a startup controller 216b, and the display 23. The communication interface 216a is also coupled to the UPSs 208 and 209 and allows for communication with the startup controller 216b. The startup controller 216b may be part of the computer 21 of the control tower 20. The output 209a supplies electrical power to the PDU 212, and the AC line input 204c supplies electrical power to an electrosurgical generator 214 through a foot switch emulator 213, which is used to provide an activation signal to the electrosurgical generator 214.

An EPO switch 211d is also located on the power ingress module 202 and allows the operator to quickly shut off power to the entire control tower 20 through the UPSs 208 and 209, as well as to the electrosurgical generator 214 through the foot switch emulator 213. Each of the UPS 208 and 209 as well as the foot switch emulator 213 is coupled to a corresponding emergency power off ("EPO") connections 211a, 211b, 211c, respectively, allowing for disconnection of the UPSs 208 and 209. When the EPO switch 211d is activated, the switches for the AC power outputs from the UPSs 208 and 209 as well as the foot switch emulator 213 open to turn off power to the control tower 20, as well as any movable arms 60 powered from the TPSC 210.

The PDU 212 powers the foot switch emulator 213 as well as various control, input devices, and communication components of the control tower 20 and the computer 21. The components of the control tower 20 powered by the output 209a include the controller 21a, the safety observer 21b, a visualization system 21c, a service router 21d, a first network switch 21e, a second network switch 21e, a light source 21g, a camera control unit 21h, and other auxiliary equipment (not shown). The first and second network switches 21e and 21f may be any suitable local area networking devices, either wired, such as ethernet, or wireless, such as WiFi. The first and second network switches 21e and 21f also interconnect the control tower 20, the surgical console 30, the robotic arm 40, and the power supply system 200.

The startup controller 216b is configured to operate in a low power mode and monitor the UPSs 208 and 209 to determine if the power supply system 200 is still connected to AC line inputs 204a, 204b, 204c. Thus, when the surgical robotic system 10 is shut down, e.g., upon completion of a surgical procedure, allowing the startup controller 216b to continue operation. In the event the AC line inputs 204a, 204b, 204c are disconnected, the startup controller 216b is also configured to control the UPSs 208 and 209 to turn off completely to preserve the battery charge.

In situations where AC line inputs 204a, 204b, 204c are disconnected from the power supply system 200 during a surgical procedure, the UPSs 208 and 209 are configured to maintain AC power to the components connected to the power supply system 200 until the startup controller 216b initiates a shutdown of all system components including the UPSs 208 and 209 under operator control, or if the UPSs 208 and 209 are about to be depleted.

If AC line inputs 204a, 204b, 204c are disconnected from the power supply system 200, the startup controller 216b is configured to monitor the UPSs 208 and 209 and detect the disconnection of AC line inputs 204a, 204b, 204c. The startup controller 216b is also configured to command the UPSs 208 and 209 to shut down following a short delay to allow for recovery from accidental disconnection.

The TPSC 210 is operational when it is connected to the AC line input 204a through the UPS 208. The TPSC 210 is configured to connect to the movable cart 60 to provide power thereto and to the robotic arm 40. The TPSC 210 is configured detect whether or not it is connected to the movable cart 60, such that electrical power is supplied to the movable cart 60 after the TPSC 210 is attached thereto. Thus, if AC line input 204a is disconnected from the TPSC 210 and the TPSC 210 is not connected to the movable cart 60, the TPSC 210 commands the UPS 208 to turn off and preserve the battery charge.

When the movable cart 60 is connected to the TPSC 210, the TPSC 210 is configured to detect which port the movable cart 60 is connected thereto and to enable the respective output from the AC/DC converter (not shown) to supply power to the movable cart 60. Similarly, when the movable cart 60 is disconnected from the TPSC 210, the TPSC 210 is configured to detect which port the movable cart 60 was disconnected from and disable the respective output from the AC/DC converter that powered the movable cart 60.

The TPSC 210 is also configured to monitor the UPS 208 and detect the loss of the AC line inputs 204a, 204b, 204c. The TPSC 210 is configured to command the UPS 208 to shut down following a short delay period to allow for recovery from accidental disconnection.

The power supply system 200 according to the present disclosure provides for a faster startup time and better preservation of the charged state of the batteries in the UPSs 208 and 209. In addition, the UPSs 208 and 209 as well as the TPSC 210 are configured to monitor power consumption. This data is collected and is used during operation of the surgical robotic system 10 and during fault detection and handling. The startup controller 216b is also configured to access this data.

The power supply system 200 is configured to operate in multiple power stages as described in further detail below. Initially, the AC line inputs 204a, 204b, 204c are connected to the power supply system 200, without the surgical robotic system 10 being set up or used for a surgical procedure. When the AC line inputs 204a and 204b are connected to the control tower 20 the UPSs 208 and 209 are charging their respective batteries. The TPSC 210 and the startup controller 216b are also operational at this time and monitor their respective UPSs 208 and 209 to determine whether the AC line inputs 204a and 204b are connected. The startup controller 216b also monitors whether a system activation signal is received, e.g., from a system activation button 24, to initiate system startup. In embodiments, the system activation button 24 may be disposed on the control tower 20 and/or the surgical console 30.

Operation of the surgical robotic system 10 occurs in three system power stages. During a first idle stage, the surgical robotic system 10 is in an idle state and the AC line inputs 204a, 204b, 204c are plugged into the control tower 20 through the power ingress module 202. During this idle state, the control tower 20 is drawing considerably less power from its AC line inputs 204a, 204b, 204c connections compared during a second active stage, namely, during the surgical operating mode. Additionally, acoustic noise emitted from the control tower 20 may be lower since cooling devices may be running slower or turned off since power consumption will be lower than during the second active stage.

During the first stage, the batteries in the UPSs 208 and 209 are charged while the surgical robotic system 10 is not being used actively. Outputs 209b of the UPS 209 are turned on and provide power to the communication interface 216a, the startup controller 216b, and display 23. The startup controller 216b also sends a signal over USB to UPSs 208 and 209 to block power output for downstream components powered by the outputs 208a, 209a, 209b, except for those specified above, namely, the communication interface 216a, the startup controller 216b, and display 23.

When the control tower 20 is in the first stage, the AC power output 208a from the UPS 208 connected to the TPSC 210 is turned off. The AC power output 209a from the UPS 209, which is connected to the PDU 212, is also turned off. The startup controller 216b, display 23, and the communication interface 216a are powered on, including the peripheral input devices (e.g., the activate button 24, touchscreen, keyboard, mouse, etc.). The USB ports on the UPSs are active to allow the UPSs to respond to any commands sent from the startup controller 216b. This allows the startup controller 216b, the display 23, and input devices coupled via the communication interface 216a to maintain enough functionality for the user to interface and fully start the surgical robotic system 10.

During the first stage as well as the later stages, if the control tower 20 is disconnected from AC line inputs 204a, 204b, 204c, software running on the startup controller 216b detects this condition and commands the UPSs 208 and 209 via the communication interface 216a to turn off to conserve the battery charge. The startup controller 216b also provides the user with alarms and messages that the control tower 20 has been disconnected from AC line inputs 204a, 204b, 204c and that the UPSs 208 and 209 will be shut off if the AC line inputs 204a, 204b, 204c are not reconnected to the control tower 20 within a preset timeout period (e.g., about 1 minute). If the AC line inputs 204a, 204b, 204c are not reconnected within the preset timeout period, then the startup controller 216b enters a third stage, which is a shutdown stage. The notifications and automatic shutdown process deals with any accidental disconnection of AC line inputs 204a, 204b, 204c from the control tower 20.

If the control tower 20 were completely disconnected from AC line inputs 204a, 204b, 204c and all of the outputs 208a, 209a, 209b from the UPSs 208 and 209, respectively, were turned off, the only load on the batteries in the UPSs 208 and 209 would be their own self-discharge, which is relatively low. This preserves the battery charge such that the control tower 20 would be ready for use the next time the control tower 20 was powered on. This would also result in less battery charge/discharge cycling, thus extending the useful life of the batteries of the UPSs 208 and 209. When power is restored to the control tower 20, by plugging the control tower 20 into AC line inputs 204a, 204b, 204c and turning the UPSs 208 and 209 on via their control panels, software running on the startup controller 216b commands the UPSs 208 and 209 to turn off the load to the TPSC 210 and PDU 212 to re-establish the idle state, namely, return to the first stage. Software running on the startup controller 216b also provides the user with information on what actions are needed to prepare the control tower 20 for surgery.

To begin using the surgical robotic system 10 for surgery, a user would press the activate button 24 on the control tower 20. This commences transition to a second active stage, during which the surgical robotic system 10 is ready to perform surgery. To transition from the first stage to the second stage, the user activates the surgical robotic system 10 through the activation button 24 and/or via system GUI. In particular, following activation of the button 24, software running on the startup controller 216*b* outputs instructions to the user on the display 23, which may request that the user perform certain steps to commence system initialization, such as by entering one or more of GUI inputs or use the keyboard/mouse/touchpad. The startup controller 216*b* is configured to confirm that the requisite steps and instructions displayed on the GUI have been followed before proceeding to the subsequent steps of the process. The startup controller 216*b* sends a first command via communication interface 216*a* to turn on AC power to the UPS 209, and in turn, to turn on equipment receiving power through PDU 212. The startup controller 216*b* also sends a second command to the UPS 208, which is connected to the TPSC 210, to turn on the TPSC 210. Once the control tower 20 is activated, the surgical robotic system 10 is in the second stage and may then used to conduct surgery.

Upon completion of the surgery, the user may enter a third stage, namely, shutdown of the surgical robotic system 10. The user activates shutdown of surgical robotic system 10 through the GUI on the display 23. In particular, software running on the startup controller 216*b* provides instructions to the user to disconnect any cables connecting the movable carts 60 and the surgical console 30 from the control tower 20 and perform any additional steps so the surgical robotic system 10 returns to the idle state of the first stage. After the startup controller 216*b* confirms that the movable carts 60 have been disconnected and other steps have been performed, the startup controller 216*b* software also sends appropriate shutdown commands to the other computing nodes in the control tower 20 and then shuts off AC power to the TPSC 210 and PDU 212 by commanding their respective UPSs 208 and 209 to turn off the appropriate outputs 208*a* and 209*a*. In embodiments, the startup controller 216*b* may also command the UPS 209 to cycle its AC power such that the startup controller 216*b*, the display 23, and communication interface 216*a* reboot, i.e., cold start. This would wipe any network configurations used during the surgical procedure during the second active stage.

It will be understood that various modifications may be made to the embodiments disclosed herein. In embodiments, the sensors may be disposed on any suitable portion of the robotic arm. Therefore, the above description should not be construed as limiting, but merely as exemplifications of various embodiments. Those skilled in the art will envision other modifications within the scope and spirit of the claims appended thereto.

What is claimed is:

1. A surgical robotic system comprising:
a plurality of movable carts, each of which includes a robotic arm; and
a control tower including:
at least one component;
a power supply system coupled to each movable cart of the plurality of movable carts, the power supply system including:
a tower power supply chassis configured to supply first direct current to each movable cart of the plurality of movable carts;

a power distribution unit configured to supply second direct current to the at least one component;
a first uninterruptable power supply coupled to the tower power supply chassis; and
a second uninterruptable power supply coupled to the power distribution unit; and
a startup controller configured to control the power supply system to transition between a plurality of power stages by selectively activating and selectively deactivating respective outputs of the first uninterruptable power supply and the second uninterruptable power supply based on a selected stage of the plurality of power stages.

2. The surgical robotic system according to claim 1, wherein the control tower further includes a display configured to display a graphical user interface and a communication interface coupled to at least one input device.

3. The surgical robotic system according to claim 2, wherein the plurality of power stages includes a first idle stage, a second active stage, and a third shutdown stage.

4. The surgical robotic system according to claim 3, wherein the second uninterruptable power supply includes a first output and a second output.

5. The surgical robotic system according to claim 4, wherein the first output of the second uninterruptable power supply is coupled to the power distribution unit and the second output of the second uninterruptable power supply is coupled to the startup controller, the display, and the communication interface.

6. The surgical robotic system according to claim 5, wherein during the first idle stage the startup controller is configured to activate an output of the first uninterruptable power supply coupled to the tower power supply chassis and the first output of the second uninterruptable power supply.

7. The surgical robotic system according to claim 6, wherein the control tower is coupled to a first alternating current input that is coupled to the first uninterruptable power supply and a second alternating current input that is coupled to the second uninterruptable power supply.

8. The surgical robotic system according to claim 7, wherein the startup controller is further configured to detect disconnection of the first alternative current input and the second alternating current input.

9. The surgical robotic system according to claim 8, wherein the startup controller is further configured to shut off the first uninterruptable power supply and the second uninterruptable power supply in response to detection of the disconnection.

10. The surgical robotic system according to claim 9, wherein the startup controller is further configured to output an alarm on the display in response to detection of the disconnection.

11. The surgical robotic system according to claim 3, wherein the startup controller is further configured to switch from the first idle stage to the second active stage in response to a user input.

12. The surgical robotic system according to claim 4, wherein during the second active stage the startup controller is further configured to activate the first output of the second uninterruptable power supply to power up the power distribution unit.

13. The surgical robotic system according to claim 4, wherein during the third shutdown stage the startup controller is further configured to display a graphical user interface of instructions for disconnecting each movable cart of the plurality of movable carts from the control tower.

14. The surgical robotic system according to claim 13, wherein during the third shutdown stage the startup controller is further configured to shutoff an output of the first uninterruptable power supply coupled to the tower power supply chassis and the first output of the second uninterruptable power supply coupled to the power distribution unit.

15. A surgical robotic system comprising:

a plurality of movable carts, each of which includes a robotic arm; and a control tower coupled to a first alternating current input and a second alternating current input, the control tower including:

at least one component;

a power supply system coupled to each movable cart of the plurality of movable carts, the power supply system including:

a tower power supply chassis configured to supply first direct current to each movable cart of the plurality of movable carts;

a power distribution unit configured to supply second direct current to the at least one component;

a first uninterruptable power supply coupled to the first alternating current input and including a first output configured to power the tower power supply chassis; and a second uninterruptable power supply coupled to the second alternating current input and including a first output configured to power the power distribution unit; and a startup controller configured to control the power supply system to transition between a first idle stage, a second active stage, and a third shut down stage by selectively activating and selectively deactivating respective outputs of the first uninterruptable power supply and the second uninterruptable power supply based on the selected stage.

16. The surgical robotic system according to claim 15, wherein the control tower further includes a display configured to display a graphical user interface and a communication interface coupled to at least one input device.

17. The surgical robotic system according to claim 16, wherein the second uninterruptable power supply includes a second output that is coupled to the startup controller, the display, and the communication interface.

18. The surgical robotic system according to claim 16, wherein the startup controller is further configured to detect disconnection of the first alternative current input and the second alternating current input.

19. The surgical robotic system according to claim 18, wherein the startup controller is further configured to shut off the first uninterruptable power supply and the second uninterruptable power supply in response to detection of the disconnection.

20. The surgical robotic system according to claim 19, wherein the startup controller is further configured to output an alarm on the display and to transition to the first idle stage.

* * * * *